(12) United States Patent
Nita et al.

(10) Patent No.: US 10,285,719 B2
(45) Date of Patent: May 14, 2019

(54) VIBRATIONAL CATHETER DEVICES AND METHODS FOR MAKING SAME

(75) Inventors: Henry Nita, Redwood City, CA (US); Jeff Sarge, Fremont, CA (US)

(73) Assignee: FLOWCARDIA, INC., Franklin Lakes, NJ (US)

( * ) Notice: Subject to any disclaimer, the term of this patent is extended or adjusted under 35 U.S.C. 154(b) by 1129 days.

(21) Appl. No.: 13/526,358

(22) Filed: Jun. 18, 2012

(65) Prior Publication Data

US 2012/0311844 A1    Dec. 13, 2012

Related U.S. Application Data

(62) Division of application No. 11/040,524, filed on Jan. 20, 2005, now Pat. No. 8,221,343.

(51) Int. Cl.
*A61B 17/22* (2006.01)
*A61B 17/00* (2006.01)

(52) U.S. Cl.
CPC .. *A61B 17/22012* (2013.01); *A61B 17/22004* (2013.01); *A61B 2017/00477* (2013.01); *A61B 2017/00526* (2013.01); *Y10T 29/49908* (2015.01); *Y10T 29/49925* (2015.01); *Y10T 29/49927* (2015.01); *Y10T 29/49929* (2015.01)

(58) Field of Classification Search
CPC ......... Y10T 29/49925; Y10T 29/49927; Y10T 29/49929
USPC ...................... 604/20–22, 275–279, 118–121
See application file for complete search history.

(56) References Cited

U.S. PATENT DOCUMENTS

| 3,296,620 A | 1/1967 | Rodda |
| 3,433,226 A | 3/1969 | Boyd |
| 3,565,062 A | 2/1971 | Kuris |

(Continued)

FOREIGN PATENT DOCUMENTS

| DE | 2256127 | 5/1974 |
| DE | 2438648 | 2/1976 |
| DE | 3821836 | 1/1990 |

(Continued)

OTHER PUBLICATIONS

Chandra Sehgal et al., Ultrasound-Assisted Thrombolysis, Investigative Radiology, 1993, vol. 28, Issue 10, pp. 939-943.

(Continued)

*Primary Examiner* — Nathan R Price
*Assistant Examiner* — Anh Bui

(57) ABSTRACT

A vibrational catheter for disrupting obstructions in lumens such as blood vessels includes an elongate flexible catheter body having a proximal end, a distal end and at least one lumen extending longitudinally therethrough, a vibrational transmission member extending longitudinally through the lumen of the catheter body and having a proximal end and a distal end, and a transition connector attached to the proximal end of the vibrational transmission member for coupling the transmission member with a vibrational energy source. The transition connector includes a bore into which the proximal end of the vibrational transmission member extends. The proximal end of the vibrational transmission member is attached within the bore of the transition connector with variable attachment forces such that the transition connector exerts a lowest amount of attachment force on an attached distal-most portion of the vibrational transmission member housed within the bore.

3 Claims, 7 Drawing Sheets

(56) References Cited

U.S. PATENT DOCUMENTS

| | | |
|---|---|---|
| 3,612,038 A | 10/1971 | Halligan et al. |
| 3,631,848 A | 1/1972 | Muller |
| 3,719,737 A | 3/1973 | Vaillancourt et al. |
| 3,739,460 A * | 6/1973 | Addis ............... H01R 4/10 138/148 |
| 3,823,717 A | 7/1974 | Pohlman |
| 3,835,690 A * | 9/1974 | Leonhardt ......... B21D 39/046 29/517 |
| 3,839,841 A | 10/1974 | Amplatz |
| 3,896,811 A | 7/1975 | Storz |
| 4,016,882 A | 4/1977 | Broadwin et al. |
| 4,033,331 A | 7/1977 | Guss et al. |
| 4,136,700 A | 1/1979 | Broadwin et al. |
| 4,337,090 A | 6/1982 | Harrison |
| 4,368,410 A | 1/1983 | Hance |
| 4,412,115 A | 10/1983 | Okuno |
| 4,417,578 A | 11/1983 | Banko |
| 4,425,115 A | 1/1984 | Wuchinich |
| 4,453,875 A | 6/1984 | Johnson, Sr. |
| 4,486,680 A | 12/1984 | Bonnet |
| 4,505,767 A | 3/1985 | Quin |
| 4,545,767 A | 10/1985 | Suzuki |
| 4,565,589 A | 1/1986 | Harrison |
| 4,565,787 A | 1/1986 | Bossle et al. |
| 4,572,184 A | 2/1986 | Stohl |
| 4,664,112 A | 5/1987 | Kensey et al. |
| 4,665,906 A | 5/1987 | Jervis |
| 4,679,558 A | 7/1987 | Kensey et al. |
| 4,700,705 A | 10/1987 | Kensey et al. |
| 4,721,117 A | 1/1988 | Mar et al. |
| 4,750,902 A | 6/1988 | Wuchinich et al. |
| 4,808,153 A | 2/1989 | Parisi |
| 4,811,743 A | 3/1989 | Stevens |
| 4,827,911 A | 5/1989 | Broadwin et al. |
| 4,838,853 A | 6/1989 | Parisi |
| 4,854,325 A | 8/1989 | Stevens |
| 4,870,953 A | 10/1989 | Donmicheal |
| 4,886,060 A | 12/1989 | Wiksell |
| 4,920,954 A | 5/1990 | Alliger |
| 4,923,462 A | 5/1990 | Stevens |
| 4,924,863 A | 5/1990 | Sterzer |
| 4,931,047 A | 6/1990 | Broadwin et al. |
| 4,936,281 A | 6/1990 | Stasz |
| 4,936,845 A | 6/1990 | Stevens |
| 5,000,185 A | 3/1991 | Yock |
| 5,015,227 A | 5/1991 | Broadwin et al. |
| 5,026,384 A | 6/1991 | Farr |
| 5,030,357 A | 7/1991 | Lowe |
| 5,046,503 A | 9/1991 | Schneiderman |
| 5,053,008 A | 10/1991 | Bajaj |
| 5,058,570 A | 10/1991 | Idemoto et al. |
| 5,076,276 A | 12/1991 | Sakurai |
| 5,091,205 A | 2/1992 | Fan |
| 5,100,423 A | 3/1992 | Fearnot |
| 5,109,859 A | 5/1992 | Jenkins |
| 5,114,414 A | 5/1992 | Buchbinder |
| 5,116,350 A | 5/1992 | Stevens |
| 5,127,917 A | 7/1992 | Niederhauser et al. |
| 5,151,105 A | 9/1992 | Kwan-Gett |
| 5,156,143 A | 10/1992 | Bocquet et al. |
| 5,163,421 A | 11/1992 | Bernstein |
| 5,171,216 A | 12/1992 | Dasse et al. |
| 5,180,363 A | 1/1993 | Idemoto et al. |
| 5,183,470 A | 2/1993 | Wettermann |
| 5,195,955 A | 3/1993 | Don Michael |
| 5,215,614 A | 6/1993 | Wijkamp et al. |
| 5,221,255 A | 6/1993 | Mahurkar |
| 5,226,421 A | 7/1993 | Frisbie et al. |
| 5,234,416 A | 8/1993 | Macaulay et al. |
| 5,238,004 A | 8/1993 | Sahatjian et al. |
| 5,242,385 A | 9/1993 | Strukel |
| 5,243,997 A | 9/1993 | Uflacker et al. |
| 5,248,296 A | 9/1993 | Alliger |
| 5,255,669 A | 10/1993 | Kubota et al. |
| 5,267,954 A | 12/1993 | Nita |
| 5,269,291 A | 12/1993 | Carter |
| 5,269,297 A | 12/1993 | Weng et al. |
| 5,269,793 A | 12/1993 | Simpson |
| 5,287,858 A | 2/1994 | Hammerslag et al. |
| 5,290,229 A | 3/1994 | Paskar |
| 5,304,115 A | 4/1994 | Pflueger |
| 5,304,131 A | 4/1994 | Paskar |
| 5,312,328 A | 5/1994 | Nita et al. |
| 5,318,014 A | 6/1994 | Carter |
| 5,318,570 A | 6/1994 | Hood et al. |
| 5,324,255 A | 6/1994 | Passafaro et al. |
| 5,324,260 A | 6/1994 | O'neill et al. |
| 5,325,860 A | 7/1994 | Seward |
| 5,326,342 A | 7/1994 | Pflueger et al. |
| 5,328,004 A | 7/1994 | Fannin et al. |
| 5,329,927 A | 7/1994 | Gardineer et al. |
| 5,341,818 A | 8/1994 | Abrams et al. |
| 5,342,292 A | 8/1994 | Nita et al. |
| 5,344,395 A | 9/1994 | Whalen et al. |
| 5,346,502 A | 9/1994 | Estabrook et al. |
| 5,362,309 A | 11/1994 | Carter |
| 5,368,557 A | 11/1994 | Nita |
| 5,368,558 A | 11/1994 | Nita |
| 5,376,084 A | 12/1994 | Bacich et al. |
| 5,378,234 A | 1/1995 | Hammerslag et al. |
| 5,380,274 A | 1/1995 | Nita |
| 5,380,316 A | 1/1995 | Aita et al. |
| 5,382,228 A | 1/1995 | Nita et al. |
| 5,383,460 A | 1/1995 | Jang |
| 5,389,096 A | 2/1995 | Aita et al. |
| 5,391,144 A | 2/1995 | Sakurai et al. |
| 5,397,293 A | 3/1995 | Alliger |
| 5,397,301 A | 3/1995 | Pflueger et al. |
| 5,405,318 A | 4/1995 | Nita |
| 5,409,483 A | 4/1995 | Campbell et al. |
| 5,417,672 A | 5/1995 | Nita et al. |
| 5,417,703 A | 5/1995 | Brown et al. |
| 5,421,923 A | 6/1995 | Clarke et al. |
| 5,427,118 A | 6/1995 | Nita et al. |
| 5,431,168 A | 7/1995 | Webster, Jr. |
| 5,431,663 A | 7/1995 | Carter |
| 5,443,078 A | 8/1995 | Uflacker |
| 5,447,509 A | 9/1995 | Mills et al. |
| 5,449,369 A | 9/1995 | Imran |
| 5,451,209 A | 9/1995 | Ainsworth et al. |
| 5,465,733 A | 11/1995 | Hinohara |
| 5,474,531 A | 12/1995 | Carter |
| 5,480,379 A | 1/1996 | La Rosa |
| 5,484,398 A | 1/1996 | Stoddard |
| 5,487,757 A | 1/1996 | Truckai et al. |
| 5,507,738 A | 4/1996 | Ciervo |
| 5,516,043 A | 5/1996 | Manna et al. |
| 5,527,273 A | 6/1996 | Manna |
| 5,540,656 A | 7/1996 | Pflueger et al. |
| 5,542,917 A | 8/1996 | Nita et al. |
| 5,562,726 A | 10/1996 | Chuter |
| 5,597,497 A | 1/1997 | Dean et al. |
| 5,597,882 A | 1/1997 | Schiller et al. |
| 5,607,421 A | 3/1997 | Jeevanandam |
| 5,611,807 A | 3/1997 | O'Boyle |
| 5,618,266 A | 4/1997 | Liprie |
| 5,626,593 A | 5/1997 | Imran |
| 5,627,365 A | 5/1997 | Chiba et al. |
| 5,649,935 A | 7/1997 | Kremer |
| 5,653,748 A | 8/1997 | Strecker |
| 5,658,282 A | 8/1997 | Daw et al. |
| 5,685,841 A | 11/1997 | Mackool |
| 5,695,460 A | 12/1997 | Siegel et al. |
| 5,695,507 A | 12/1997 | Auth et al. |
| 5,715,825 A | 2/1998 | Crowley |
| 5,720,724 A | 2/1998 | Ressemann et al. |
| 5,728,062 A | 3/1998 | Brisken |
| 5,738,100 A | 4/1998 | Yagami et al. |
| 5,797,876 A | 8/1998 | Spears et al. |
| 5,816,923 A | 10/1998 | Milo et al. |
| 5,827,203 A | 10/1998 | Nita |
| 5,827,971 A | 10/1998 | Hale et al. |
| 5,830,222 A | 11/1998 | Makower |
| 5,846,218 A | 12/1998 | Brisken et al. |

(56) References Cited

U.S. PATENT DOCUMENTS

| | | | |
|---|---|---|---|
| 5,893,838 A | 4/1999 | Daoud et al. |
| 5,895,397 A | 4/1999 | Jang |
| 5,902,287 A | 5/1999 | Martin |
| 5,904,667 A | 5/1999 | Falwell |
| 5,916,192 A | 6/1999 | Nita et al. |
| 5,916,912 A | 6/1999 | Ames et al. |
| 5,935,142 A | 8/1999 | Hood |
| 5,935,144 A | 8/1999 | Estabrook |
| 5,937,301 A | 8/1999 | Gardner et al. |
| 5,944,737 A | 8/1999 | Tsonton |
| 5,957,882 A | 9/1999 | Nita et al. |
| 5,957,899 A | 9/1999 | Spears et al. |
| 5,964,223 A | 10/1999 | Baran |
| 5,967,984 A | 10/1999 | Chu et al. |
| 5,971,949 A | 10/1999 | Levin et al. |
| 5,976,119 A | 11/1999 | Spears et al. |
| 5,989,208 A | 11/1999 | Nita |
| 5,989,275 A | 11/1999 | Estabrook et al. |
| 5,997,497 A | 12/1999 | Nita et al. |
| 6,004,280 A | 12/1999 | Buck |
| 6,007,499 A | 12/1999 | Martin et al. |
| 6,007,514 A | 12/1999 | Nita |
| 6,015,431 A | 1/2000 | Thornton et al. |
| 6,019,785 A | 2/2000 | Strecker |
| 6,022,309 A | 2/2000 | Celliers et al. |
| 6,024,764 A | 2/2000 | Schroeppel |
| 6,029,671 A | 2/2000 | Stevens et al. |
| 6,030,357 A | 2/2000 | Daoud et al. |
| 6,042,605 A | 3/2000 | Martin et al. |
| 6,051,010 A | 4/2000 | DiMatteo |
| 6,113,558 A | 9/2000 | Rosenschein et al. |
| 6,123,698 A | 9/2000 | Spears et al. |
| 6,142,971 A | 11/2000 | Daoud et al. |
| 6,149,596 A | 11/2000 | Bancroft |
| 6,159,176 A | 12/2000 | Broadwin et al. |
| 6,165,127 A | 12/2000 | Crowley |
| 6,165,188 A | 12/2000 | Saadat et al. |
| 6,179,809 B1 | 1/2001 | Khairkhahan et al. |
| 6,180,059 B1 | 1/2001 | Divino, Jr. et al. |
| 6,190,353 B1 | 2/2001 | Makower et al. |
| 6,206,842 B1 | 3/2001 | Tu |
| 6,210,356 B1 | 4/2001 | Anderson et al. |
| 6,217,543 B1 | 4/2001 | Anis et al. |
| 6,217,565 B1 | 4/2001 | Cohen |
| 6,217,588 B1 * | 4/2001 | Jerger ............. A61B 17/22012 606/127 |
| 6,221,015 B1 | 4/2001 | Yock |
| 6,231,546 B1 | 5/2001 | Milo et al. |
| 6,231,587 B1 | 5/2001 | Makower |
| 6,235,007 B1 | 5/2001 | Divinio, Jr. et al. |
| 6,241,692 B1 | 6/2001 | Tu et al. |
| 6,241,703 B1 | 6/2001 | Levin et al. |
| 6,248,087 B1 | 6/2001 | Spears et al. |
| 6,277,084 B1 | 8/2001 | Abele et al. |
| 6,283,983 B1 | 9/2001 | Makower et al. |
| 6,287,271 B1 | 9/2001 | Dubrul et al. |
| 6,287,285 B1 | 9/2001 | Michal et al. |
| 6,287,317 B1 | 9/2001 | Makower et al. |
| 6,296,620 B1 | 10/2001 | Gesswein |
| 6,302,875 B1 | 10/2001 | Makower et al. |
| 6,302,891 B1 | 10/2001 | Nadal |
| 6,309,358 B1 | 10/2001 | Okubo |
| 6,315,741 B1 | 11/2001 | Martin et al. |
| 6,315,754 B1 | 11/2001 | Daoud et al. |
| 6,346,192 B2 | 2/2002 | Buhr et al. |
| 6,352,561 B1 | 3/2002 | Leopold et al. |
| 6,379,378 B1 | 4/2002 | Werneth et al. |
| 6,387,109 B1 | 5/2002 | Davison |
| 6,387,324 B1 | 5/2002 | Patterson et al. |
| 6,394,956 B1 | 5/2002 | Chandrasekaran et al. |
| 6,398,736 B1 | 6/2002 | Seward |
| 6,409,673 B2 | 6/2002 | Yock |
| 6,416,533 B1 | 7/2002 | Gobin et al. |
| 6,423,026 B1 | 7/2002 | Gesswein et al. |
| 6,427,118 B1 | 7/2002 | Suzuki |
| 6,433,464 B2 | 8/2002 | Jones |
| 6,434,418 B1 | 8/2002 | Neal et al. |
| 6,450,975 B1 | 9/2002 | Brennan et al. |
| 6,454,757 B1 | 9/2002 | Nita |
| 6,454,997 B1 | 9/2002 | Divino, Jr. et al. |
| 6,484,052 B1 | 11/2002 | Visuri et al. |
| 6,491,707 B2 | 12/2002 | Makower |
| 6,494,891 B1 | 12/2002 | Cornish et al. |
| 6,494,894 B2 | 12/2002 | Mirarchi |
| 6,500,141 B1 | 12/2002 | Irion et al. |
| 6,508,781 B1 * | 1/2003 | Brennan ............. A61B 17/22012 600/467 |
| 6,508,784 B1 | 1/2003 | Shu |
| 6,511,458 B2 | 1/2003 | Milo et al. |
| 6,524,251 B2 | 2/2003 | Rabiner et al. |
| 6,533,766 B1 | 3/2003 | Patterson et al. |
| 6,544,215 B1 | 4/2003 | Bencini et al. |
| 6,547,754 B1 | 4/2003 | Evans et al. |
| 6,551,337 B1 | 4/2003 | Rabiner et al. |
| 6,554,846 B2 | 4/2003 | Hamilton et al. |
| 6,555,059 B1 | 4/2003 | Myrick et al. |
| 6,558,502 B2 | 5/2003 | Divino, Jr. et al. |
| 6,562,031 B2 | 5/2003 | Chandrasekaran et al. |
| 6,573,470 B1 | 6/2003 | Brown et al. |
| 6,576,807 B1 | 6/2003 | Brunelot et al. |
| 6,582,387 B2 | 6/2003 | Derek et al. |
| 6,589,253 B1 | 7/2003 | Cornish et al. |
| 6,595,989 B1 | 7/2003 | Schaer |
| 6,596,235 B2 | 7/2003 | Divino, Jr. et al. |
| 6,602,467 B1 | 8/2003 | Divino, Jr. et al. |
| 6,602,468 B2 | 8/2003 | Patterson et al. |
| 6,605,217 B2 | 8/2003 | Buhr et al. |
| 6,607,698 B1 | 8/2003 | Spears et al. |
| 6,613,072 B2 | 9/2003 | Lau et al. |
| 6,613,280 B2 | 9/2003 | Myrick et al. |
| 6,615,062 B2 | 9/2003 | Ryan et al. |
| 6,616,617 B1 | 9/2003 | Ferrera et al. |
| 6,622,542 B2 | 9/2003 | Derek et al. |
| 6,623,448 B2 | 9/2003 | Slater |
| 6,635,017 B1 | 10/2003 | Moehring et al. |
| 6,650,923 B1 | 11/2003 | Lesh et al. |
| 6,652,547 B2 | 11/2003 | Rabiner et al. |
| 6,660,013 B2 | 12/2003 | Rabiner |
| 6,676,900 B1 | 1/2004 | Divino, Jr. et al. |
| 6,682,502 B2 | 1/2004 | Bond et al. |
| 6,685,657 B2 | 2/2004 | Jones |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,810 B2 | 2/2004 | Peacock, III et al. |
| 6,702,748 B1 | 3/2004 | Nita et al. |
| 6,702,750 B2 | 3/2004 | Yock |
| 6,719,715 B2 | 4/2004 | Newman et al. |
| 6,719,725 B2 | 4/2004 | Milo et al. |
| 6,729,334 B1 | 5/2004 | Baran |
| 6,733,451 B2 | 5/2004 | Rabiner et al. |
| 6,758,846 B2 | 7/2004 | Goble et al. |
| 6,761,698 B2 | 7/2004 | Shibata et al. |
| 6,855,123 B2 | 2/2005 | Nita |
| 6,866,670 B2 | 3/2005 | Rabiner et al. |
| 6,936,025 B1 | 8/2005 | Evans et al. |
| 6,936,056 B2 | 8/2005 | Nash et al. |
| 6,942,620 B2 | 9/2005 | Nita et al. |
| 6,942,677 B2 | 9/2005 | Nita et al. |
| 6,955,680 B2 | 10/2005 | Satou et al. |
| 7,004,173 B2 | 2/2006 | Sparks et al. |
| 7,004,176 B2 | 2/2006 | Lau |
| 7,056,294 B2 | 6/2006 | Khairkhahan et al. |
| 7,131,983 B2 | 11/2006 | Murakami |
| 7,137,963 B2 | 11/2006 | Nita et al. |
| 7,150,853 B2 | 12/2006 | Lee et al. |
| 7,166,098 B1 | 1/2007 | Steward et al. |
| 7,220,233 B2 | 5/2007 | Nita et al. |
| 7,267,650 B2 | 9/2007 | Chow et al. |
| 7,297,131 B2 | 11/2007 | Nita |
| 7,335,180 B2 | 2/2008 | Nita et al. |
| 7,384,407 B2 | 6/2008 | Rodriguez et al. |
| 7,393,338 B2 | 7/2008 | Nita |
| 7,421,900 B2 | 9/2008 | Karasawa et al. |

(56) References Cited

U.S. PATENT DOCUMENTS

| | | |
|---|---|---|
| 7,425,198 B2 | 9/2008 | Moehring et al. |
| 7,494,468 B2 | 2/2009 | Rabiner et al. |
| 7,503,895 B2 | 3/2009 | Rabiner et al. |
| 7,540,852 B2 | 6/2009 | Nita et al. |
| 7,594,926 B2 | 9/2009 | Linder et al. |
| 7,604,608 B2 | 10/2009 | Nita et al. |
| 7,621,902 B2 | 11/2009 | Nita et al. |
| 7,621,929 B2 | 11/2009 | Nita et al. |
| 7,686,783 B2 | 3/2010 | Jenson et al. |
| 7,771,358 B2 | 8/2010 | Moehring et al. |
| 7,775,994 B2 | 8/2010 | Lockhart |
| 7,776,025 B2 | 8/2010 | Bobo, Jr. |
| 7,819,013 B2 | 10/2010 | Chan et al. |
| 7,850,623 B2 | 12/2010 | Griffin et al. |
| 7,896,183 B2 | 3/2011 | Mckenzie |
| 7,935,108 B2 | 5/2011 | Baxter et al. |
| 7,938,819 B2 | 5/2011 | Kugler et al. |
| 7,955,293 B2 | 6/2011 | Nita et al. |
| 8,043,251 B2 | 10/2011 | Nita et al. |
| 8,083,727 B2 | 12/2011 | Kugler et al. |
| 8,092,513 B2 | 1/2012 | Khosravi et al. |
| 8,133,236 B2 | 3/2012 | Nita |
| 8,221,343 B2 | 7/2012 | Nita et al. |
| 8,226,566 B2 | 7/2012 | Nita |
| 8,226,701 B2 | 7/2012 | Glynn |
| 8,246,643 B2 | 8/2012 | Nita |
| 8,506,519 B2 | 8/2013 | Nita |
| 8,608,677 B2 | 12/2013 | Motyer |
| 8,617,096 B2 | 12/2013 | Nita et al. |
| 8,632,560 B2 | 1/2014 | Pal et al. |
| 8,647,296 B2 | 2/2014 | Moberg et al. |
| 8,690,819 B2 | 4/2014 | Nita et al. |
| 8,790,291 B2 | 7/2014 | Nita et al. |
| 8,974,446 B2 | 3/2015 | Nguyen et al. |
| 9,060,894 B2 | 6/2015 | Wubbeling |
| 9,107,590 B2 | 8/2015 | Hansmann et al. |
| 9,265,520 B2 | 2/2016 | Nita |
| 9,282,984 B2 | 3/2016 | Nita |
| 9,314,258 B2 | 4/2016 | Nita et al. |
| 9,757,260 B2 | 9/2017 | Greenan |
| 9,770,250 B2 | 9/2017 | Nita et al. |
| 2002/0077643 A1 | 6/2002 | Rabiner |
| 2003/0009153 A1 | 1/2003 | Brisken et al. |
| 2003/0036705 A1 | 2/2003 | Hare et al. |
| 2003/0125620 A1 | 7/2003 | Satou et al. |
| 2003/0199817 A1 | 10/2003 | Thompson et al. |
| 2003/0216732 A1 | 11/2003 | Truckai et al. |
| 2003/0225332 A1 | 12/2003 | Okada |
| 2004/0138570 A1 | 7/2004 | Nita et al. |
| 2004/0167507 A1 | 8/2004 | Nita et al. |
| 2004/0204670 A1 | 10/2004 | Nita et al. |
| 2005/0033311 A1 | 2/2005 | Guldfeldt et al. |
| 2005/0113688 A1 | 5/2005 | Nita et al. |
| 2005/0215946 A1 | 9/2005 | Hansmann et al. |
| 2005/0222557 A1 | 10/2005 | Baxter et al. |
| 2005/0228286 A1 | 10/2005 | Messerly et al. |
| 2006/0206039 A1 | 9/2006 | Wilson et al. |
| 2006/0264759 A1 | 11/2006 | Moehring et al. |
| 2006/0264809 A1 | 11/2006 | Hansmann et al. |
| 2007/0037119 A1 | 2/2007 | Pal et al. |
| 2007/0260172 A1 | 11/2007 | Nita |
| 2008/0071343 A1 | 3/2008 | Mayberry et al. |
| 2008/0108937 A1 | 5/2008 | Nita |
| 2008/0208084 A1 | 8/2008 | Horzewski et al. |
| 2008/0221506 A1 | 9/2008 | Rodriguez et al. |
| 2008/0228111 A1 | 9/2008 | Nita |
| 2008/0287804 A1 | 11/2008 | Nita |
| 2010/0023037 A1 | 1/2010 | Nita et al. |
| 2011/0105960 A1 | 5/2011 | Wallace |
| 2011/0130834 A1 | 6/2011 | Wilson et al. |
| 2011/0237982 A1 | 9/2011 | Wallace |
| 2011/0313328 A1 | 12/2011 | Nita |
| 2012/0130475 A1 | 5/2012 | Shaw |
| 2012/0330196 A1 | 12/2012 | Nita |
| 2014/0243712 A1 | 8/2014 | Humayun et al. |
| 2016/0128717 A1 | 5/2016 | Nita |
| 2016/0271362 A1 | 9/2016 | Van Liere |

FOREIGN PATENT DOCUMENTS

| | | |
|---|---|---|
| DE | 8910040 | 1/1990 |
| DE | 4042435 | 8/1991 |
| EP | 0005719 | 12/1979 |
| EP | 0316789 | 5/1989 |
| EP | 0376562 | 7/1990 |
| EP | 0379156 | 7/1990 |
| EP | 0394583 | 10/1990 |
| EP | 0443256 | 8/1991 |
| EP | 0541249 | 5/1993 |
| EP | 0316796 | 11/1995 |
| EP | 0820728 | 1/1998 |
| EP | 1323481 A2 | 7/2003 |
| GB | 1106957 | 3/1968 |
| JP | 61-272045 A | 12/1986 |
| JP | SHO61-272045 | 12/1986 |
| JP | 01099547 | 4/1989 |
| JP | 2-71510 | 5/1990 |
| JP | U03067608 | 7/1991 |
| JP | 7-500752 | 1/1995 |
| JP | 2007116260 | 5/1995 |
| JP | 10216140 | 8/1998 |
| JP | 2000-291543 | 10/2000 |
| JP | 2001104356 | 4/2001 |
| JP | 2001321388 | 11/2001 |
| JP | 2002186627 | 7/2002 |
| JP | 2005-253874 | 9/2005 |
| JP | 2006086822 | 3/2006 |
| JP | 2006-522644 A | 10/2006 |
| JP | 2007520255 A | 7/2007 |
| WO | WO87/05793 | 10/1987 |
| WO | WO89006515 | 7/1989 |
| WO | 9001300 A1 | 2/1990 |
| WO | WO09001300 | 2/1990 |
| WO | WO9004362 | 5/1990 |
| WO | WO9107917 | 6/1991 |
| WO | WO92011815 | 7/1992 |
| WO | WO93008750 | 5/1993 |
| WO | WO93016646 | 9/1993 |
| WO | WO94012140 | 6/1994 |
| WO | WO94014382 | 7/1994 |
| WO | WO95008954 | 4/1995 |
| WO | WO95009571 | 4/1995 |
| WO | WO 95/15192 | 6/1995 |
| WO | WO96035469 | 11/1996 |
| WO | 9705739 A1 | 2/1997 |
| WO | WO 97/21462 | 6/1997 |
| WO | WO97045078 | 12/1997 |
| WO | 9827874 A1 | 7/1998 |
| WO | 9827895 A1 | 7/1998 |
| WO | 9835721 A2 | 8/1998 |
| WO | WO98/052637 | 11/1998 |
| WO | WO9851224 | 11/1998 |
| WO | WO99025412 | 5/1999 |
| WO | WO0053341 A1 | 9/2000 |
| WO | WO00/67830 | 11/2000 |
| WO | WO03039381 | 5/2003 |
| WO | WO04012609 | 2/2004 |
| WO | 2004093736 A2 | 11/2004 |
| WO | WO04112888 | 12/2004 |
| WO | 2005053769 A2 | 6/2005 |
| WO | WO 2006/049593 | 5/2006 |
| WO | 2007084762 A2 | 7/2007 |
| WO | 2008140796 A1 | 11/2008 |
| WO | 2009083904 A2 | 7/2009 |
| WO | 2010063795 A1 | 6/2010 |
| WO | 2012068046 A2 | 5/2012 |
| WO | 2014022716 A2 | 2/2014 |

OTHER PUBLICATIONS http://www.merriam-webster.com/dictionary/couple, definition of the term coupled retrieved on, May 18, 2013.

(56) References Cited

OTHER PUBLICATIONS

Margaret Fyfe et al., Mast cell degranulation and increased vascular permeability induced by 'therapeutic' ultrasound in the rate ankle joint, Br. J. exp. Path., 1984, vol. 65, pp. 671-676.
Extended European Search Report for Patent Application No. 06718204.8, dated May 30, 2012.
Health Care Without Harm [report], Non-Incineration Medical Waste Treatment Technologies, "Irradiation, biological, and other technologies: E-beam, biological, and sharps treatment systems", Chapter 9., Aug. 2001, pp. 69-74.
Siegel et al., In Vivo Ultrasound Arterial Recanalization Atherosclerotic Total Occlusions, Journal of the American College of Cardiology, Feb. 1990, vol. 15, Issue 2, pp. 345-351.
Calhoun et al., "Electron-Beam Systems for Medical Device Sterilization", downloaded from web on Oct. 8, 2002 <http://www.devicelink.com/mpb/archive/97/07/002.html> 7 pages total.
"E-Beam Theory" RDI-IBA Technology Group, downloaded from web on Oct. 8, 2002 <http://www.e-beamrdi/EbeamTheory.htm> 2 pages total.
"What is Electron Beam Curing?" downloaded from web on Nov. 14, 2002, 4 pages total. <http://www.ms.oml.gov/researchgroups/composites/new%20orccmt%20pages/pages/ebwha>.
"Irradiation, Biological, and Other Technologies: E-beam, Biological, and Sharps Treatment Systems", Non-Incineration Medical Waste Treatment Technologies, Aug. 2001, Chapter 9, pp. 69-74, Health Care Without Harm, Washington, DC.
Noone, D.: Experimental and Numerical Investigation of Wire Waveguides for Therapeutic Ultrasound Angioplasty. M.Eng. Dublin City University. 2008.
Extended European Search Report dated Mar. 5, 2012 for European Application No. 12153606.4-1269.
Japanese Office Action for Japanese Application No. 2010-134566, dated Mar. 2, 2012.
Supplemental European Search Report dated Nov. 5, 2009 for European Application No. EP03766931.
International Search Report dated Oct. 28, 2003 for PCT Application No. PCT/US2003/023468.
Extended European Search Report dated Mar. 22, 2012 for European Application No. EP11188799.
International Search Report dated Dec. 23, 2005 for PCT Application No. PCT/US2004/019378.

\* cited by examiner

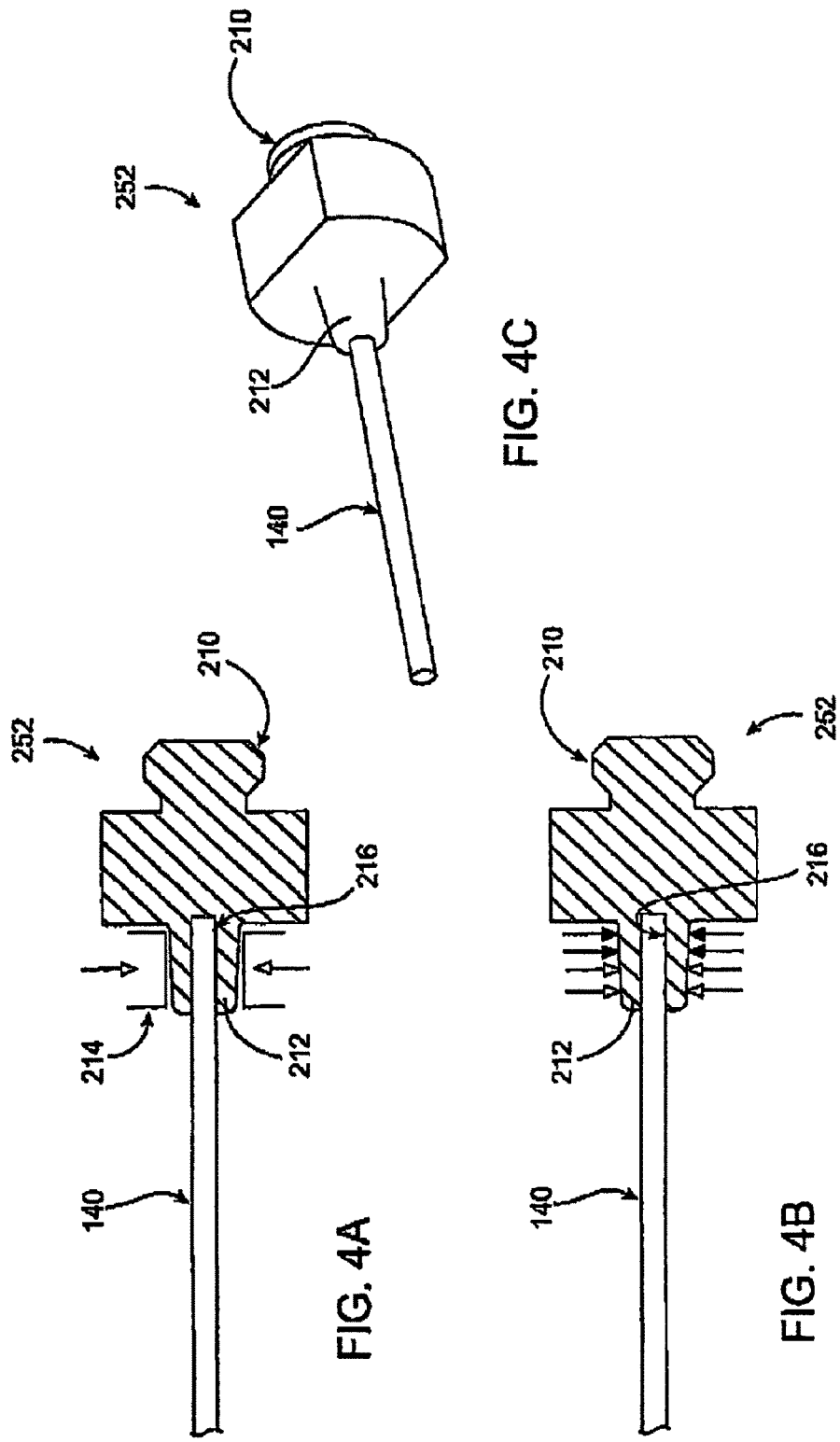

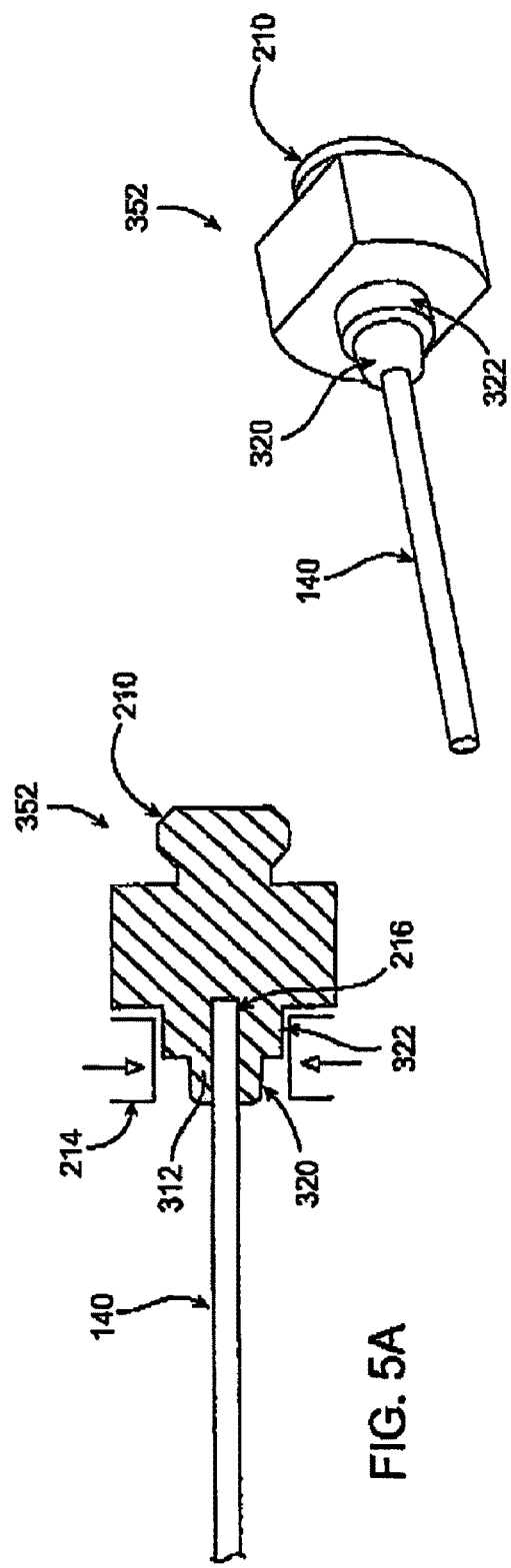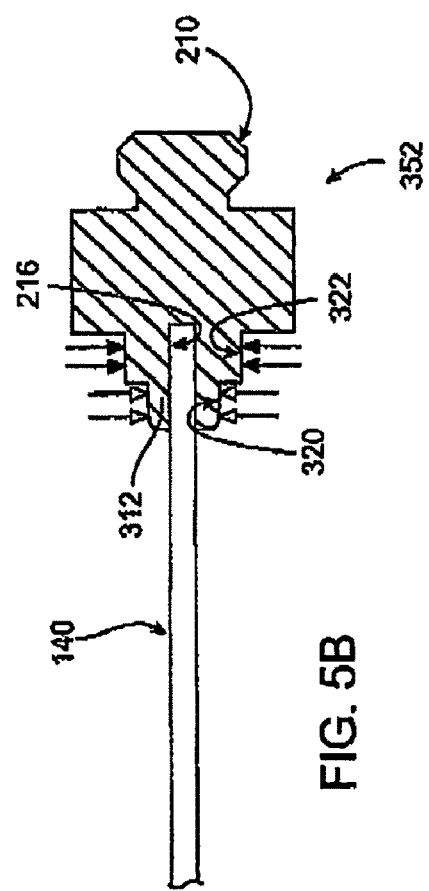

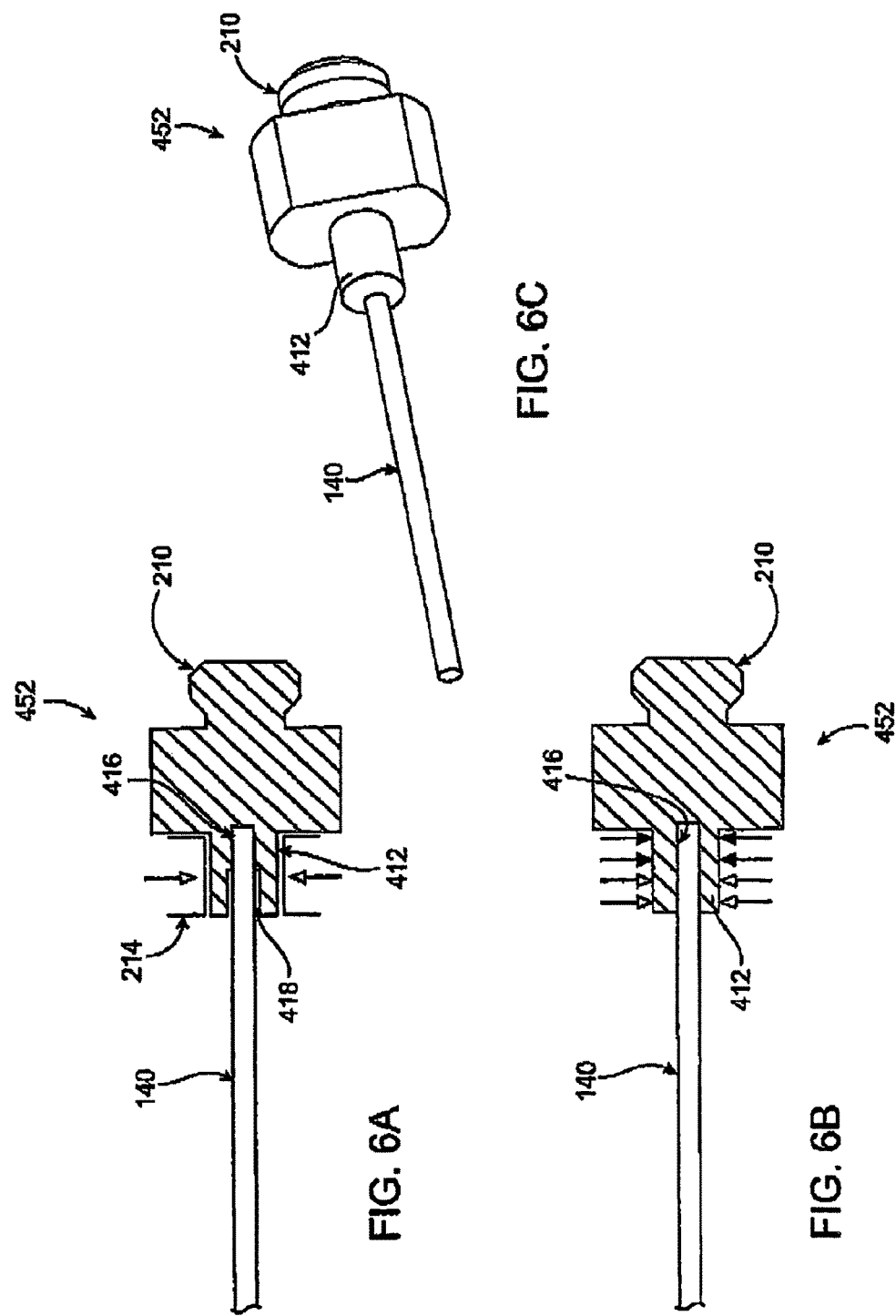

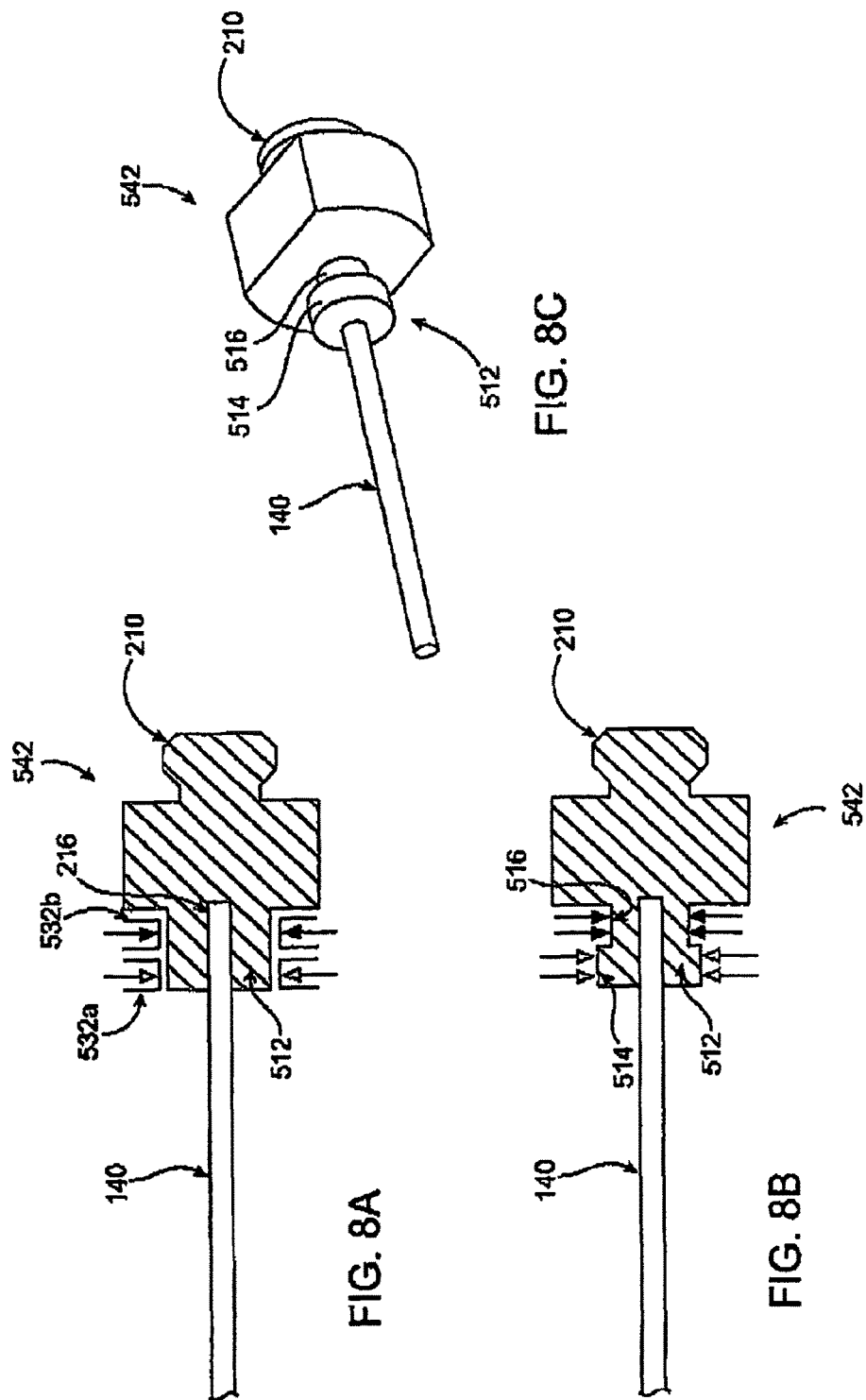

VIBRATIONAL CATHETER DEVICES AND METHODS FOR MAKING SAME

CROSS-REFERENCE TO RELATED APPLICATIONS

This application is a divisional of U.S. patent application Ser. No. 11/040,524, filed Jan. 20, 2005. This application is related to the following: U.S. patent application Ser. No. 10/229,371, filed Aug. 26, 2002, entitled "Ultrasound Catheter for Disrupting Blood Vessel Obstructions;" U.S. patent application Ser. No. 10/345,078, filed Jan. 14, 2003, entitled "Ultrasound Catheter and Methods for Making and Using Same;" U.S. patent application Ser. No. 10/375,903, filed Feb. 26, 2003, entitled "Ultrasound Catheter Apparatus;" U.S. patent application Ser. No. 10/410,617, filed Apr. 8, 2003, entitled "Improved Ultrasound Catheter Devices and Methods;" U.S. patent application Ser. No. 10/722,209, filed Nov. 24, 2003, entitled "Steerable Ultrasound Catheter;" and U.S. patent application Ser. No. 10/927,966, filed Aug. 26, 2004, entitled "Improved Ultrasound Catheter Devices and Methods." The full disclosures of all of the above-listed patent applications are all hereby incorporated by reference.

BACKGROUND OF THE INVENTION

The present invention relates generally to medical devices and methods. More specifically, the present invention relates to vibrational catheter devices and methods for treating occlusive intravascular lesions.

Catheters employing various types of vibration transmitting members have been successfully used to ablate or otherwise disrupt obstructions in blood vessels. Specifically, ablation of atherosclerotic plaque or thromboembolic obstructions from peripheral blood vessels such as the femoral arteries has been particularly successful. Various vibrational catheter devices have been developed for use in ablating or otherwise removing obstructive material from blood vessels. For example, U.S. Pat. Nos. 5,267,954 and 5,380,274, issued to an inventor of the present invention and hereby incorporated by reference, describe ultrasound catheter devices for removing occlusions. Other examples of ultrasonic ablation devices for removing obstructions from blood vessels include those described in U.S. Pat. No. 3,433,226 (Boyd), U.S. Pat. No. 3,823,717 (Pohlman, et al.), U.S. Pat. No. 4,808,153 (Parisi), 4,920,954 (Alliger, et al.), as well as other patent publications WO87-05739 (Cooper), WO89-06515 (Bernstein, et al.), WO90-0130 (Sonic Needle Corp.), EP316789 (Don Michael, et al.), DE3,821,836 (Schubert) and DE2438648 (Pohlman). While many vibrational catheters have been developed, however, improvements are still being pursued.

Typically, a vibrational catheter system for ablating occlusive material includes three basic components: an vibration energy generator, a transducer, and a vibrational catheter. The generator converts line power into a high frequency current that is delivered to the transducer. The transducer contains piezoelectric crystals which, when excited by the high frequency current, expand and contract at high frequency. These small, high-frequency expansions (relative to an axis of the transducer and the catheter) are amplified by the transducer horn into vibrational energy. The vibrations are then transmitted from the transducer through the vibrational catheter via a vibrational transmission member (or wire). The transmission member transmits the vibrational energy to the distal end of the catheter where the energy is used to ablate or otherwise disrupt a vascular obstruction.

To effectively reach various sites for treatment of intravascular occlusions, vibrational catheters of the type described above typically have lengths of about 150 cm or longer. To permit the advancement of such vibrational catheters through small and/or tortuous blood vessels such as the aortic arch, coronary vessels, and peripheral vasculature of the lower extremities, the catheters (and their respective ultrasound transmission wires) must typically be sufficiently small and flexible. Also, due to attenuation of ultrasound energy along the long, thin, ultrasound transmission wire, a sufficient amount of vibrational energy must be applied at the proximal end of the wire to provide a desired amount of energy at the distal end.

One continuing challenge in developing vibrational catheters for treating vascular occlusions is to provide adequate vibrational energy at the distal end of a catheter device while simultaneously minimizing stress on the vibrational transmission wire in the area where it connects with the transducer. Typically, the vibrational transmission wire is coupled with the transducer via some kind of connector. A portion of the transmission wire immediately adjacent the connector is often put under great stress and strain when sufficient vibrational energy is applied to provide the desired vibration at the distal end of the catheter. This stress and strain can cause overheating and unwanted wear and tear of the transmission member, thus leading to wire breakage and a shortened useful life of the catheter device.

Some vibrational catheter devices include one or more absorption members where the proximal end of the vibrational transmission wire attaches to a transducer connector. For example, one such absorption member is described in U.S. Pat. No. 5,382,228. Such absorption members, however, may have drawbacks, in that they may be prone to coming loose and disconnecting from the transducer connector, and would thus become a loosely moving body within the catheter, disrupting vibrational energy transmission and reducing the catheter's efficacy.

Therefore, a need exists for improved vibrational catheter devices and methods that provide ablation and/or disruption of obstructions in lumens, such as vascular lumens. Ideally, such vibrational catheters would provide a desired level of power at a distal end of the device while also preventing or reducing stress and strain placed on the proximal end of the vibrational transmission member. Also ideally, such devices would be easily manufactured and have as few moving parts as possible in the area of connection of the transmission member with the transducer connector. At least some of these objectives will be met by the present invention.

BRIEF SUMMARY OF THE INVENTION

In one aspect of the present invention, a vibrational catheter for disrupting obstructions in lumens such as blood vessels includes an elongate flexible catheter body having a proximal end, a distal end and at least one lumen extending longitudinally therethrough, a vibrational transmission member extending longitudinally through the lumen of the catheter body and having a proximal end and a distal end, and a transition connector attached to the proximal end of the vibrational transmission member for coupling the transmission member with a vibrational energy source. The transition connector includes a bore into which the proximal end of the vibrational transmission member extends. The proximal end of the vibrational transmission member is attached within the bore of the transition connector with variable attachment forces such that the transition connector exerts a lowest amount of attachment force on an attached distal-most portion of the vibrational transmission member housed within the bore.

In some embodiments, the vibrational energy source comprises a transducer, such as but not limited to an ultrasound transducer. In some embodiments, the transition connector may comprise multiple pieces attached together, while in other embodiments the transition connector comprises a one-piece extrusion. In one embodiment, the proximal connection member of the transition connector comprises threads, which are complementary to threads on the vibrational energy source. Alternatively, any other suitable connection device may be used.

In some embodiments, the transition connector comprises a distal portion tapered proximally to distally, the distal portion extending from a proximal terminus of the bore to the opening of the bore. In such embodiments, the vibrational transmission member may be attached within the bore by crimping the tapered distal portion of the transition connector so as to apply greater crimping force to a wider, proximal portion of the distal portion than to a narrower, distal portion of the distal portion. In alternative embodiments, the transition connector comprises a distal portion including a first stepped portion having a first radius and extending distally from a proximal terminus of the bore and a second stepped portion having a second radius smaller than the first radius and extending from a distal end of the first stepped portion to the distal opening of the bore. In these latter embodiments, the vibrational transmission member may be attached within the bore by crimping the first stepped portion, thus applying greater crimping force to the first stepped portion than the second stepped portion.

In another alternative embodiment, the bore comprises a first stepped portion having a first radius and extending distally from a proximal terminus of the bore and a second stepped portion having a second radius greater than the first radius and extending from a distal end of the first stepped portion to the distal opening of the bore. Optionally, in such an embodiment, the vibrational transmission member may be attached within the bore by crimping the transition connector, thus applying greater crimping force to the first stepped portion than the second stepped portion. In some cases, a space exists between the transmission member and the second stepped portion of the bore before crimping, and the space closes during crimping.

In another aspect of the present invention, a vibrational catheter for disrupting obstructions in lumens such as blood vessels includes an elongate flexible catheter body having a proximal end, a distal end and at least one lumen extending longitudinally therethrough, a vibrational transmission member extending longitudinally through the lumen of the catheter body and having a proximal end and a distal end, and a transition connector. The transition connector includes a proximal connection member for attaching the transition connector to a vibrational energy source and a bore having an opening in a distal end of, and extending into, the transition connector, for accepting the proximal end of the vibrational transmission member. The proximal end of the vibrational transmission member extends into and is attached within the distal bore of the transition connector such that the transition connector exerts a greater amount of attachment force on an attached proximal-most portion of the transmission member than on an adjacent portion of the transmission member immediately distal to the proximal-most portion. Various embodiments of this catheter may include any of the features described above.

In another aspect of the present invention, a method for making a vibrational catheter for disrupting obstructions in lumens such as blood vessels includes inserting a proximal end of a vibrational transmission member into a bore in a transition connector and crimping at least part of the transition connector to attach the proximal end of the vibrational transmission member within the bore. In this method, a variable amount of crimping force is applied to attach the vibrational transmission member within the bore, so that the transition connector exerts a lowest amount of attachment force on an attached distal-most portion of the vibrational transmission member housed within the bore.

In some embodiments, crimping is performed with a crimping tool having a contact surface parallel with the vibrational transmission member, and the greater amount of crimping force is applied via a shaped portion of the transition connector overlying the bore. In alternative embodiments, crimping is performed with a crimping tool having a contact surface parallel with the vibrational transmission member, and the greater amount of crimping force is applied via a shaped bore. In another alternative embodiment, crimping is performed with a tapered crimping tool having a contact surface that contacts a proximal portion of the transition connector overlying the bore before contacting a more distal portion of the transition connector overlying the bore. Alternatively, crimping may performed with two crimping members, a more proximal crimping member applying greater force than a more distal crimping member. In another alternative embodiment, crimping involves crimping a first portion of the transition connector overlying the proximal-most portion of the transmission member with a crimping tool, moving the crimping tool distally along the transition connector, and crimping a second portion of the transition connector overlying the adjacent portion of the transmission member.

These and other aspects and embodiments of the present invention are described in further detail below, in reference to the attached drawing figures.

BRIEF DESCRIPTION OF THE DRAWINGS

FIGS. 4A and 4B are cross-sectional side views of a proximal portion of a vibrational transmission member coupled with a transition connector for connecting to a vibrational energy source, according to an embodiment of the present invention;

FIG. 4C is a perspective view of the vibrational transmission member and transition connector of FIGS. 4A and 4B;

FIGS. 5A and 5B are cross-sectional side views of a proximal portion of a vibrational transmission member coupled with a transition connector for connecting to a vibrational energy source, according to an alternative embodiment of the present invention;

FIG. 5C is a perspective view of the vibrational transmission member and transition connector of FIGS. 5A and 5B;

FIGS. 6A and 6B are cross-sectional side views of a proximal portion of a vibrational transmission member coupled with a transition connector for connecting to a vibrational energy source, according to an alternative embodiment of the present invention;

FIG. 6C is a perspective view of the vibrational transmission member and transition connector of FIGS. 6A and 6B;

FIGS. 8A and 8B are cross-sectional side views of a proximal portion of a vibrational transmission member coupled with a transition connector for connecting to a vibrational energy source, according to an alternative embodiment of the present invention; and FIG. 8C is a perspective view of the vibrational transmission member and transition connector of FIGS. 8A and 8B.

DETAILED DESCRIPTION OF THE INVENTION

Vibrational catheter devices and methods of the present invention provide for disruption of occlusions in blood vessels. The vibrational catheter devices generally include a catheter body, a vibrational energy transmission member disposed within the catheter body, and a distal head coupled with the vibrational transmission member and disposed at or near the distal end of the catheter body. The vibrational transmission member transmits vibrational energy, such as ultrasound energy, from a proximal vibrational energy source, such as an ultrasound transducer, to the distal head, causing the head to vibrate and, thus, disrupt vascular occlusions. A number of features of such vibrational catheter devices are described more fully below.

Figure 1:
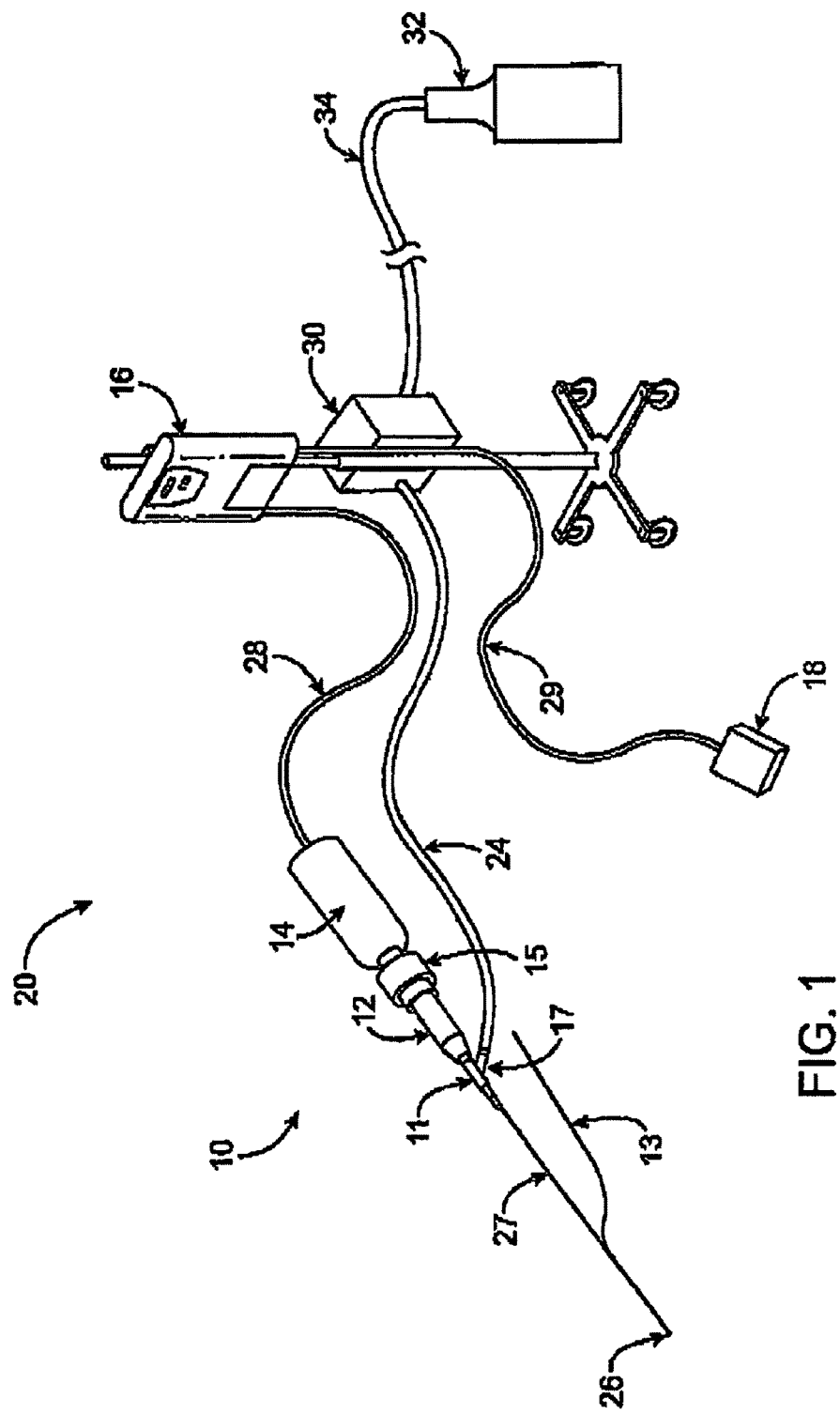
FIG. 1 is a perspective view of a vibrational catheter system, according to an embodiment of the present invention.

Referring now to FIG. 1, one embodiment of a vibrational catheter system 20 suitably includes a vibrational catheter device 10 and a vibrational energy generator 16. Catheter device 10 suitably includes a distal head 26 for disrupting occlusions, a catheter body 27, and a proximal end knob 12 for coupling catheter device 10 with a vibrational energy transducer 14. Vibrational energy transducer 14 is coupled with ultrasound generator 16 via a connector 28, and generator is coupled with a foot-actuated on/off switch 18 via another connector 29. Generator 16 provides vibrational energy to transducer 14 and, thus, to vibrational catheter 10. Catheter device 10 further includes a vibrational transmission member (or "wire"—not shown) that extends through the catheter body 27 and transmits energy from the transducer 14 to the distal head 26. Some embodiments of device 10 include a rapid exchange guidewire 13 and guidewire port, while other embodiments include a proximal guidewire port for over the wire guidewire delivery. In some embodiments, transducer 14 further includes a securing device 15 for enhancing coupling of catheter 10 to transducer 14. The various components of system 20 may be coupled via any suitable means. Connectors 28, 29 may comprise an electric cord or cable or any other suitable connecting devices for coupling on/off switch 18, generator 16 and transducer 14. In an alternative embodiment, on/off switch 18 is located on generator 16.

In addition to proximal knob 12, vibrational catheter device 10 may include one or more other various components, such as a Y-connector 11 including a fluid inlet port 17 (or aperture) for passage of irrigation fluid. Inlet port 17 may be removably coupled with an irrigation tube 24, which in one embodiment may be coupled with a fluid refrigeration (or "fluid cooling") device 30. Refrigeration device 30 may, in turn, be coupled with a fluid container 32 via a connector tube 34. This irrigation apparatus may be used for introducing one or more fluids into catheter device 10. Fluid may be used to cool any part of the device, such as the vibrational transmission member, thus helping reduce wear and tear of device 10. In some embodiments, fluid inlet port 17 is located farther proximally on proximal knob 12, to allow fluid to be applied within knob 12. In some embodiments, refrigerated fluid is used, while in other embodiments irrigation fluid may be kept at room temperature. In various embodiments, oxygen supersaturated fluid, lubricious fluid, or any other suitable fluid or combination of fluids may be used, and again, such fluids may be refrigerated or kept room temperature. In an alternative embodiment to that shown in FIG. 1, refrigeration device 30 and fluid container 32 are combined in one device.

Generally, catheter device 10 may include any suitable number of side-arms or ports for passage of a guidewire, application of suction, infusing and/or withdrawing irrigation fluid, dye and/or the like, or any other suitable ports or connections. Also, vibrational catheters 10 of the present invention may be used with any suitable proximal devices, such as any suitable transducer 14, generator 16, coupling device(s) and/or the like. Therefore, the exemplary embodiment shown in FIG. 1 and any following descriptions of proximal apparatus or systems for use with vibrational catheters 10 should not be interpreted to limit the scope of the present invention as defined in the appended claims.

Figure 2:
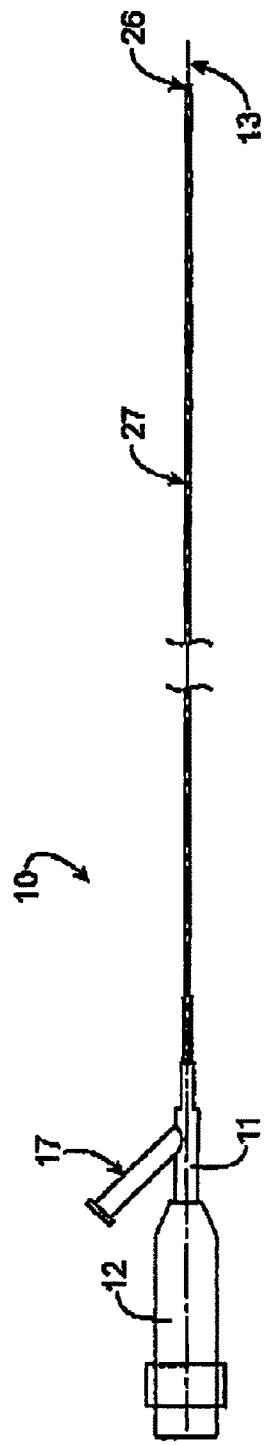
FIG. 2 is a side view of a vibrational catheter device, according to an embodiment of the present invention.

Referring now to FIG. 2, an enlarged view of catheter device 10 is shown. Proximal knob 12, Y-connector 11, inlet port 17, catheter body 27, distal head 26 and guidewire 13 are all shown. Catheter body 27 is generally a flexible, tubular, elongate member, having any suitable diameter and length for reaching a vascular occlusion for treatment. In one embodiment, for example, catheter body 27 preferably has an outer diameter of between about 0.5 mm and about 5.0 mm. In other embodiments, as in catheters intended for use in relatively small vessels, catheter body 27 may have an outer diameter of between about 0.25 mm and about 2.5 mm. Catheter body 27 may also have any suitable length. As discussed briefly above, for example, some vibrational catheters 10 have a length in the range of about 150 cm. However, any other suitable length may be used without departing from the scope of the present invention. Examples of catheter bodies similar to those which may be used in the present invention are described in U.S. Pat. Nos. 5,267,954 and 5,989,208, which were previously incorporated herein by reference.

Features of the present invention may be applied to any of a number of vibrational catheter devices. For more detailed description of exemplary vibrational catheter devices, reference may be made to U.S. patent application Ser. Nos. 10/229,371, 10/345,078, 10/375,903, 10/410,617, 10/722, 209 and 0/927,966, which were all previously incorporated by reference. In various alternative embodiments, aspects of the present invention may be applied to any other suitable catheter devices.

Figure 3:
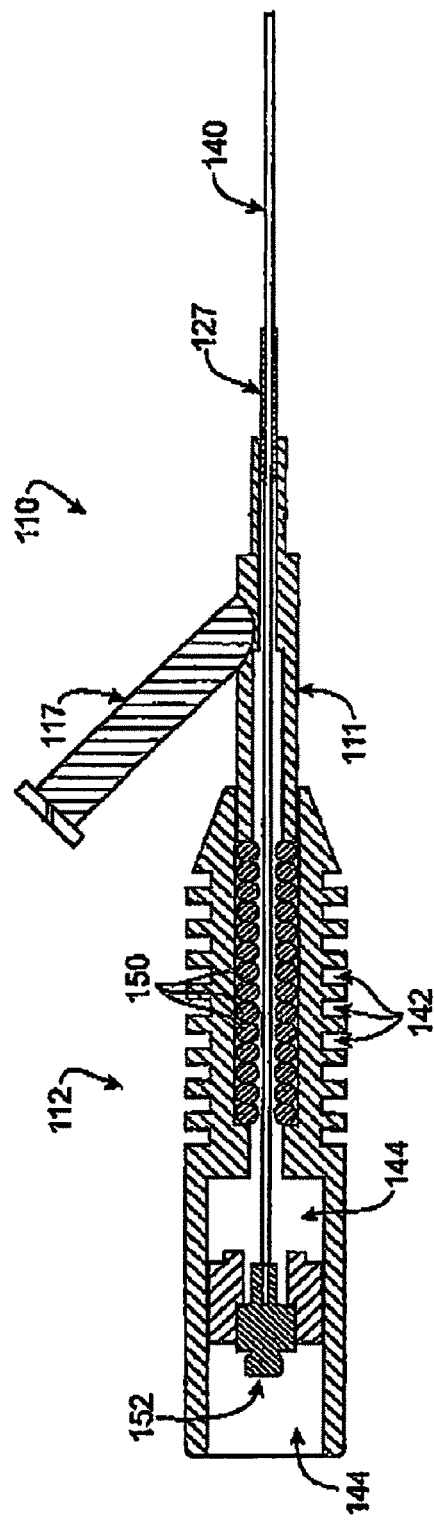
FIG. 3 is cross-sectional side view of a proximal portion of a vibrational catheter device having heat dissipation means, according to an embodiment of the present invention.

Referring now to FIG. 3, a proximal portion of one embodiment of a vibrational catheter device 110 is shown in cross-section. An ultrasound transmission wire 140 extends from a transition connector 152 distally to a distal end (not shown) of catheter device 110. A catheter body 127 of device 110 is shown only in part, whereas catheter body 127 typically extends distally to (or near) the distal end of device 110. Catheter device 110 also includes a proximal knob 112 (or "housing"), having an inner bore 144 in which transition connector 152, a portion of vibrational transmission member 140 and one or more vibration absorption members 150 reside. Knob 112 is coupled with a Y-connector 111, which includes a fluid inlet port 117 (or aperture), and Y-connector 111 is coupled with catheter body 127.

In various embodiments, knob 112 may suitably include one or more surface features 142 for increasing the overall surface area of the outer surface of knob 112. Increased surface area enhances the ability of knob 112 to dissipate heat generated by vibrational transmission member 140 out of catheter device 110. Surface features 142 may have any suitable size or shape, such as ridges, jags, undulations, grooves or the like, and any suitable number of surface features 142 may be used. Additionally, knob 112 may be made of one or more heat dissipating materials, such as aluminum, stainless steel, any other conductive metal(s), or any suitable non-metallic conductive material(s).

In most embodiments, vibrational transmission member 140, wire, or wave guide extends longitudinally through a lumen of catheter body 127 to transmit vibrational energy from a transducer (not shown), connected to the proximal end of proximal knob 112, to the distal end of catheter device 110. Vibrational transmission member 140 may be formed of any material capable of effectively transmitting vibrational energy from the transducer, such as an ultrasound transducer, to the distal end of catheter body 127, including but not limited to metals such as pure titanium or aluminum, or titanium or aluminum alloys. Again, additional details of vibrational transmission members 140 may be found in the patent applications incorporated by reference above. Similarly, reference may be made to the incorporated patent applications for descriptions of knob 112, transition connector 152, vibration absorption members 150, Y-connector 111 and the like. For example, knob 112 and other features are described in detail in U.S. patent application Ser. No. 10/722,209, which was previously incorporated by reference.

Vibrational transmission member 140 typically passes from transition connector 152, through bore 144 and Y-connector 111, and then through catheter body 127. Fluid inlet port 117 is in fluid communication with a lumen in Y-connector, which is in fluid communication with a lumen extending through catheter body 127. Thus, fluid introduced into fluid inlet port 117 is typically free to flow into and through catheter body 127 to contact vibrational transmission member 140. Fluid may flow out of catheter body 127 through apertures in the distal head (not shown) or through any other suitable apertures or openings, such as apertures located in catheter body 127 itself. Any suitable fluid may be passed through fluid inlet port 117 and catheter body 127, such as refrigerated fluid, lubricious fluid, super-saturated saline or contrast/saline mixture, or the like. Cooling and/or lubricating vibrational transmission member 140 may reduce friction and/or wear and tear of vibrational transmission member 140, thus prolonging the useful life of vibrational catheter device 110 and enhancing its performance.

Additionally, the temperature and flow rate of a coolant liquid may be specifically controlled to maintain the temperature of vibrational transmission member 140 at a desired temperature within its optimal working range. In particular, in embodiments of the invention where vibrational transmission member 140 is formed of a metal alloy which exhibits optimal physical properties (e.g. super elasticity) within a specific range of temperatures, the temperature and flow rate of coolant liquid infused through fluid inlet port 117 may be specifically controlled to maintain the temperature of vibrational transmission member 140 within a range of temperatures at which it demonstrates its most desirable physical properties. For example, in embodiments of the invention where vibrational transmission member 140 is formed of a shape memory alloy which exhibits superelasticity when in its martensite state, but which loses super-elasticity as it transitions to an austenite state, it will be desirable to adjust the temperature and flow rate of the coolant liquid infused through fluid inlet port 117 to maintain the shape memory alloy of vibrational transmission member 140 within a temperature range at which the alloy will remain in its martensite state and will not transition to an austenite state. The temperature at which such shape memory alloys transition from a martensite state to an austenite state is known as the "martensite transition temperature" of the material. Thus, in these embodiments, the fluid infused through port 117 will be at such temperature, and will be infused at such rate, as to maintain the shape memory alloy of vibrational transmission member 140 below its martensite transition temperature.

As mentioned above, in one embodiment, a super-saturated fluid may be used. Use of such fluids may enhance cavitation of an occlusion, help prevent unwanted tissue damage and/or the like. Such fluids are described, for example, in U.S. Pat. Nos. 6,676,900, 6,622,542, 6,613,280, 6,607,698, 6,605,217, 6,602,468, 6,602,467, 6,596,235, 6,582,387, 6,576,807, 6,558,502, 6,555,059, 6,533,766, 6,454,997, 6,387,324, 6,346,192, 6,315,754, 6,248,087, 6,235,007, 6,180,059, 6,142,971, 6,123,698, 6,030,357, 5,976,119, 5,957,889, 5,893,838 and 5,797,876, which are hereby incorporated by reference. In another embodiment, a mixture of contrast dye and saline may be used to achieve the same or similar results.

With reference now to FIGS. 4A-4C, one embodiment of a proximal portion of a vibrational transmission member 140 and a transition connector 252 for connecting to a vibrational transducer is shown. Transition connector 252 includes a proximal connection member 210 for attaching to a vibrational transducer, such as an ultrasound transducer. Connector 252 also includes a tapered distal portion 212 with a bore 216 extending into it from the distal end of connector 252. The proximal end of vibrational transmission member 140 extends into bore 216, and distal portion 212 is crimped down onto the proximal end of transmission member 140, using a crimping device 214 (crimping motion designated by hollow-tipped arrows in FIG. 4A). As shown in FIG. 4A, crimping force is applied to tapered distal portion 212 via crimping device 214 oriented parallel with a longitudinal axis along the length of ultrasound transmission member 140. Thus, crimping device 214 contacts and begins applying force to a proximal end of distal portion 212 before contacting and applying force to a distal end of distal portion 212.

By crimping distal portion 212 using the technique just described, and referring now to FIG. 4B, greater crimping force (solid-tipped arrows) is applied by distal portion 212 against an attached proximal-most portion of transmission member 140 than is applied against an immediately adjacent more-distal portion of transmission member 140 (hollow-tipped arrows). By applying this variable crimping force to transmission member 140, distal portion 212 of transition connector 252 absorbs vibrational motion occurring near its distal end, thus reducing stress on the transmission member 140 at the point where it enters bore 216. This stress reduction helps reduce wear and tear on transmission member 140, thus extending the useful life of the catheter device.

FIG. 4C shows an attached vibrational transmission member 140 and transition connector 252. In various embodiments, transition connector 252 may be a one-piece member or may alternatively include two or more pieces attached together. Proximal connection member 210 may include any suitable attachment means for removably attaching transition connector 252 to a transducer, such as but not limited to threads for screwing into complementary threads on the transducer or a snap-fit connector.

With reference now to FIGS. 5A-5C, an alternative embodiment of a transition connector 352 includes a proximal connection member 210 and a distal portion 312 having a bore 216, a proximal step 322 and a distal step 320. Proximal step 322 has a greater outer diameter than distal step 320. Thus, when crimping force is applied to distal portion 312, as shown in FIG. 5A (hollow-tipped arrows), crimping device 214 contacts only proximal step 322. Force is indirectly applied to distal step 320 through proximal step 322, but as depicted in FIG. 5B, greater force (solid-tipped arrows) is applied to transmission member 140 via proximal step 322 than via distal step 320. This variable crimping force allows distal step 320 to absorb vibrations of transmission member 140, thus reducing wear and tear.

FIG. 5C is a perspective view of the assembled transition connector 352 and vibrational transmission member 140.

Referring now to FIGS. 6A-6C, an alternative embodiment of a transition connector 452 includes a proximal connection member 210 and a distal portion 412 having a bore 416 with a widened distal opening 418. Referring to FIG. 6A, to attach transition connector 452 to vibrational transmission member 140, crimping force (hollow-tipped arrows) is applied via crimping device 214 oriented approximately along a longitudinal axis of the catheter. As shown in FIG. 6B, in this embodiment, crimping force closes widened distal opening 418 around transmission member 140. The crimping process thus applies less force (hollow-tipped arrows) against transmission member 140 via the distal-most part of distal portion 412 than via an immediately adjacent, more proximal part of distal portion (solid-tipped arrows). Again, this variable crimping force allows for vibrational absorption at the distal end of transition connector 452, thus reducing stress on vibrational transmission member.

FIG. 6C is a perspective view of the assembled transition connector 452 and vibrational transmission member 140.

Figure 7A:
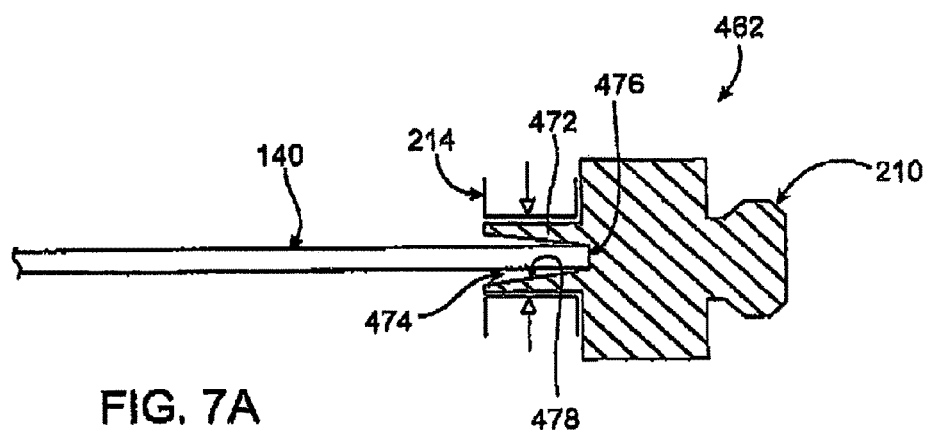
FIGS. 7A and 7B are cross-sectional side views of a proximal portion of a vibrational transmission member coupled with a transition connector for connecting to a vibrational energy source, according to an alternative embodiment of the present invention.
Figure 7B:
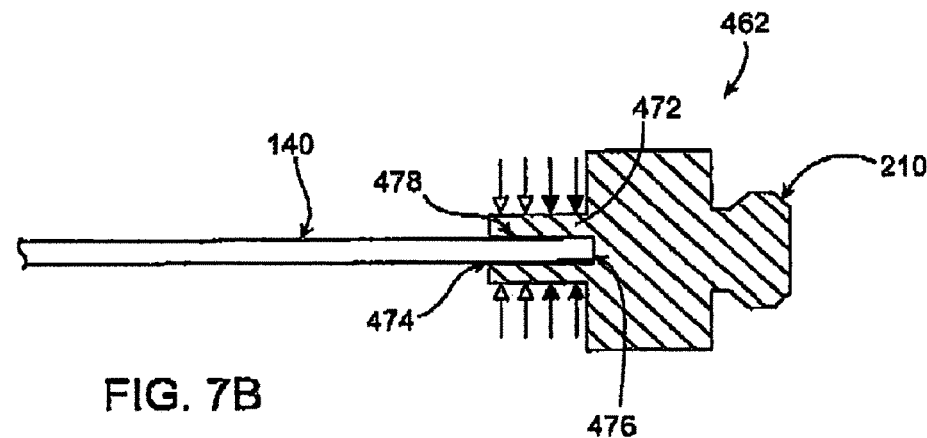

Referring now to FIGS. 7A-7C, an alternative embodiment of a transition connector 462 includes a proximal connection member 210 and a distal portion 472 having a bore 478 that widens from its proximal terminus 476 to a widened distal opening 474. The widened distal opening 474 forms a space between opening 474 and transmission member 140. Referring to FIG. 7A, to attach transition connector 462 to vibrational transmission member 140, crimping force (hollow-tipped arrows) is applied via crimping device 214 oriented approximately along a longitudinal axis of the catheter. As shown in FIG. 7B, crimping force closes widened distal opening 474 around transmission member 140. The crimping process thus applies less force (hollow-tipped arrows) against transmission member 140 via the distal-most part of distal portion 472 than via an immediately adjacent, more proximal part of distal portion (solid-tipped arrows). Again, this variable crimping force allows for vibrational absorption at the distal end of transition connector 462, thus reducing stress on vibrational transmission member.

With reference now to FIGS. 8A-8C, an alternative embodiment of a transition connector 542 includes a proximal connection member 210 and a distal portion 512 having a bore 216. Referring to FIG. 8A, to attach transition connector 542 to vibrational transmission member 140, crimping force is applied via a distal crimping member 532a (hollow-tipped arrows) and a proximal crimping member 532b. Crimping members 532 may be part of one crimping device but controlled separately, or alternatively they may be two separate devices. In an alternative embodiment, one crimping member 532 may be used but applied sequentially to proximal and distal parts of distal portion 512. In any case, the force applied to distal portion 512 via proximal crimping member 532b (solid-tipped arrows) is greater than the force applied to distal portion 512 via distal crimping member 532a (hollow-tipped arrows).

As shown in FIG. 8B, the variably applied force (solid-tipped and hollow-tipped arrows) causes distal portion 512 to be more compressed near its proximal end, thus forming a proximal step 516 with a smaller outer diameter and a distal step 514 with a greater outer diameter. In turn, more crimping force is applied against transmission member 140 by proximal step 516 than by distal step 514, thus allowing for vibrational absorption by distal step 514.

FIG. 8C is a perspective view of the assembled transition connector 542 and vibrational transmission member 140, showing proximal step 516 and distal step 514 of distal portion 512.

Although the invention has been described above with specific reference to various embodiments and examples, it should be understood that various additions, modifications, deletions and alterations may be made to such embodiments without departing from the spirit or scope of the invention. Accordingly, it is intended that all reasonably foreseeable additions, deletions, alterations and modifications be included within the scope of the invention as defined in the following claims.

What is claimed is:

1. A method for making a vibrational catheter, comprising:
  providing a transition connector of the catheter having a bore defining an open distal end and a closed proximal end;
  inserting a proximal end of a vibrational transmission member into the open end of the bore in the transition connector of the catheter;
  crimping at least part of the transition connector to attach the proximal end of the vibrational transmission member within the bore adjacent the closed proximal end of the bore, wherein a variable amount of crimping force is applied to attach the transmission member within the bore, such that the transition connector exerts a lowest amount of attachment force on an attached distal-most portion of the vibrational transmission member housed within the bore,
    wherein crimping is performed with a crimping tool having a contact surface parallel with the vibrational transmission member along an entire contact length during crimping, and wherein the greater amount of crimping force is applied via a shaped portion of the transition connector overlying the bore, wherein the shaped portion exists in the transition connector before being crimped; and
  inserting the vibrational transmission member through a plurality of 0-rings located in a catheter handle.

2. A method for making a vibrational catheter, comprising:

providing a transition connector of the catheter having a bore defining an open distal end and a closed proximal end;

inserting a proximal end of a vibrational transmission member into the open end of the bore in the transition connector of the catheter;

crimping at least part of the transition connector to attach the proximal end of the vibrational transmission member within the bore adjacent the closed proximal end of the bore, wherein a variable amount of crimping force is applied to attach the transmission member within the bore, such that the transition connector exerts a lowest amount of attachment force on an attached distal-most portion of the vibrational transmission member housed within the bore, wherein crimping is performed with a crimping tool having a contact surface parallel with the vibrational transmission member over a length experiencing the variable amount of crimping force, and wherein the greater amount of crimping force is applied via a shaped bore, the shaped bore having a larger inner diameter at a distal-most portion of the bore than a proximal portion of the bore before being crimped; and inserting the vibrational transmission member through a plurality of 0-rings located in a catheter handle.

3. A method for making a vibrational catheter, comprising:

providing a transition connector of the catheter having a bore defining an open distal end and a closed proximal end;

inserting a proximal end of a vibrational transmission member into the open end of the bore in the transition connector of the catheter;

crimping at least part of the transition connector to attach the proximal end of the vibrational transmission member within the bore adjacent the closed proximal end of the bore, wherein a variable amount of crimping force is applied to attach the transmission member within the bore, such that the transition connector exerts a lowest amount of attachment force on an attached distal-most portion of the vibrational transmission member housed within the bore, wherein crimping is performed with a linearly tapered crimping tool having a contact surface that contacts a proximal portion of the transition connector overlying the bore before contacting a more distal portion of the transition connector overlying the bore; and inserting the vibrational transmission member through a plurality of 0-rings located in a catheter handle.

\* \* \* \* \*